United States Patent [19]
Lahr et al.

[11] Patent Number: 5,958,979
[45] Date of Patent: Sep. 28, 1999

[54] STABILIZED MEDICAMENTS CONTAINING THYROID HORMONES

[75] Inventors: Wolfgang Lahr; Andrea Friese; Guido Weickgenannt, all of Berlin, Germany

[73] Assignee: Henning Berlin GmbH & Co., Berlin, Germany

[21] Appl. No.: 09/051,376

[22] PCT Filed: Sep. 30, 1996

[86] PCT No.: PCT/EP96/04274

§ 371 Date: Apr. 8, 1998

§ 102(e) Date: Apr. 8, 1998

[87] PCT Pub. No.: WO97/16178

PCT Pub. Date: May 9, 1997

[30] Foreign Application Priority Data

Oct. 27, 1995 [DE] Germany .......................... 195 41 128

[51] Int. Cl.$^6$ .......................... A61K 31/195; A61K 9/20
[52] U.S. Cl. .......................... 514/567; 424/451; 424/464; 424/484; 424/488; 514/557; 562/447; 562/602
[58] Field of Search ..................... 424/451, 464, 424/484, 486, 488; 514/567; 562/447

[56] References Cited

U.S. PATENT DOCUMENTS 4,154,820  5/1979  Simoons ................. 424/175

5,225,204  7/1993  Chen et al. ................. 424/484

FOREIGN PATENT DOCUMENTS 2191695  6/1997  United Kingdom ........... 31/55

OTHER PUBLICATIONS

Chemical Patents Indesx, Basic Abstracts Journal, Sec. B, Derwent Publications, Ltd., London (Jun. 19, 1985), No. 85–102741/17; JP 0048937 A.

Chemical Abstracts, vol. 121, No. 18, Abstract Number: 213005, 1994.

Chemical Patents Index, Documentation Abstracts Journal, Sec. B, Derwent Publications, Ltd., London (Jun. 19, 1991). No. 91–112628/16; JP 3052814 A.

Chemical Patents Index, Basic Abstracts Journal, Sec. D. Derwent Publications, Ltd., London (Sep. 21, 1988). No. 88–209830/30; JP 3146829 A.

*Primary Examiner*—Richard L. Raymond
*Attorney, Agent, or Firm*—Ladas & Parry

[57] ABSTRACT

The present invention relates to stabilized medicaments containing thyroid hormone the stabilizing component of which is sodium thiosulfate in a mass ratio of thyroid hormone to sodium thiosulfate of 1:0.1 to 1:50 and processes for preparing such medicaments.

18 Claims, No Drawings

STABILIZED MEDICAMENTS CONTAINING THYROID HORMONES

This application is a 371 of PCT/EP96/04274, filed Sep. 30, 1996.

The present invention relates to stabilised medicaments containing thyroid hormones and processes for preparing the same.

Thyroid hormones within the meaning of the present invention are hormones suitable for therapeutic application, especially those of natural or synthetic origin bearing two to four iodine atoms in the molecule such as levothyroxin, liothyronin, dextrothyroxin, triiodoacetic acid, thyroid (dried thyroid), thyroglobulin, diiodotyrosin, and analogues and salts thereof.

Thyroid hormones of the above-mentioned type are used therapeutically for thyroid diseases of various origins, especially hyperthyroidism, hypothyrosis, iodine deficiency and related secondary diseases but also for prophylactic substitution both as monosubstances and in combination with each other or with other active ingredients such as iodine salts. Levothyroxin and liothyrinin, which are used in the form of their salts or as free acids, have attained special significance in this respect.

Thyroid hormones of the above type, especially the salts commonly used as medicaments, are very susceptible to temperature, humidity and oxidation. They are decomposed by various reaction mechanisms. In addition, they react with many of the pharmaceutical excipients commonly used so that it is difficult to prepare medicaments wherein the active ingredient remains effective for a sufficient period of time under regular storage conditions within the limits applicable for pharmaceutical agents, i.e. without special precautions.

In the normal central European climate (climatic zone I, i.e. a mean temperature of 21° C.), conventional levothyroxin sodium tablets, for example, remain active for a maximum of three years at the still tolerable level of at least 90% of the active ingredients declared, but at higher temperature and humidity levels (climatic zones II to IV) stability cannot be maintained over this period of time. This disadvantageously cuts the time span during which the medicament may be sold. A decrease of the active ingredient level by 10% until the end of marketability which is tolerated for the climatic zone I must also be regarded as critical, because, as a rule, little is known about the type and activity of the resulting degradation products, especially with regard to their toxicity.

There has been no lack of attempts to stabilise thyroid hormones in medicament form, especially levothyroxin for oral administration to humans which determines any therapy. U.S. Pat. No. 5,225,204 (Chen et al.), for example, proposes to prepare a levothyroxin-sodium complex together with polyvinyl pyrrolidone and a cellulose component for stabilisation. Without the degree of stabilisation being explained in greater detail in this publication, the process described there has the disadvantage of a costly process for preparing the complex. Especially the use of organic solvents is considered disadvantageous both for cost and ecological reasons.

It was the object of the present invention to prepare medicaments containing thyroid hormones in such a manner that their stability is guaranteed for more than three years in the climatic zone I and at least three years in the climatic zones II to IV without special storage precautions and to provide a simple, ecologically safe process for preparing the same.

According to general consensus, the climatic zones are defined as follows ("The regulation of medicaments within the European Community", Volume III, EC Commission, Jan. 1989):

TABLE 1

| Climatic conditions | Zone I moderate | Zone II Mediterranean (subtropical) | Zone III hot/dry or hot/moderate humidity | Zone IV very/hot humid |
|---|---|---|---|---|
| Annual mean temperature | <20.5° C. | 20.5–24° C. | >24° C. | >24° C. |
| Kinetic mean temperature (virtual temp.) | 21° C. | 26° C. | 31° C. | 31° C. |
| Average of relative humidity p.a. | 45% | 60% | 40% | 70% |

The countries of the European Union are in zones I and II.

It has now been found that sodium thiosulfate which is used in medicine as an antagonist in case of cyanide intoxication is suitable to stabilise thyroid hormone preparations in such a manner that their stability is surprisingly increased in comparison with conventional preparations. Within the meaning of toxicity, sodium thiosulfate is considered non-toxic. According to the ADI list (acceptable daily intake) a daily intake of up to 700 μg/kg bodyweight is permitted. This would correspond to up to an amount of 49 mg/day for a 70 kg adult (Martindale, the Extra Pharmacopoeia, London 1982, pages 392–393).

The inventors have found that a weight ratio of the thyroid hormone to be stabilised to sodium thiosulfate in the range of 1:0.1 to 1:50 at fluid boundaries is suitable to bring about the stabilising effect without the recommended upper limit of approx. 50 mg of sodium thiosulfate as maximum daily dosage being exceeded.

Since the dosage of thyroid hormones is selected depending on each patient and the degree of the disease (levothyroxin, for example, generally at less than 25 to about 300 μg per form of administration and day for long-term therapy and up to 1 mg for diagnostic purposes), it is inevitable that the absolute quantities of the stabilising sodium thiosulfate vary, the lower limit of 1:0.1 advantageously being used for higher dosages and the upper limit of 1:5 being suitable for lower dosages.

It is a special embodiment of the subject matter of the invention that the sodium thiosulfate is introduced into a matrix which reacts in a slightly acidic to slightly alkaline manner in a pH range of 5.5 to 9, preferably in a slightly alkaline manner, when dissolved or suspended in an aqueous medium so as to protect the sodium thiosulfate itself against degradation. The matrix of medicaments generally consists of excipients such as diluents, binders, rupturing agents, flow regulators, lubricants and slip additives, optionally flavour improving agents, preservatives, colouring agents or film-forming substances some of which may still contain a few contaminations which react in a slightly acidic manner and may have a decomposing effect on the sodium thiosulfate.

Substances which are harmless under pharmacological and toxicological aspects such as those described in pertinent pharmacopoeias or in the "Handbook of Pharmaceutical Excipients" of the American Pharmaceutical Association/Pharmaceutical Society of Great Britain,. 1986, or in H. P. Fiedler's "Lexikon der Hilfsstoffe für Pharmazie, Kosmetik und angrenzende Gebiete" (lexicon of excipients for pharmaceuticals, cosmetics and adjacent fields), Editio Cantor Verlag, Aulendorf 1989, are used as matrix-forming excipients to formulate medicaments containing thyroid (thyroid hormones). The excipients used in the compositions according to the invention are a selection of potentially suitable excipients such as lactose, microcrystalline cellulose and other celluloses and cellulose derivatives, starch of various origins and starch derivatives or starches which have undergone special treatment, highly dispersed silica and common lubricants and slip agents. Some of these, for example starch, may contain contaminations which react in a slightly acidic manner and have a decomposing effect on the sodium thiosulfate used in accordance with the invention, especially when water is used in preparing the medicament, for example in wet granulation of a tablet mixture. In such a case, a component neutralising the acidic components is added to the matrix. Suitable components of this kind are other physiologically safe excipients such as buffering substances, but also alkaline salts such as sodium carbonate or small quantities of lye, e.g. caustic lye of soda. Since the quantity of components having a neutralising and/or buffering effect depends on the amount of acidic contaminations in the other excipients, the actual amount needed must be determined experimentally so as to obtain a pH after addition which is 5.5 to 9 and preferably 6 to 8.5 in the aqueous medium of the matrix dissolved or suspended therein.

The use of sodium thiosulfate according to the invention to stabilise thyroid hormones in the type of medicaments listed above permits simple production processes. In such processes, sodium thiosulfate in a dissolved state is added to the matrix mixture containing the active ingredient in order to obtain an intimate mixture. This is even more important since both the active ingredient and the stabiliser are used in very low dosages.

In order to prepare tablet granules, for example, the sodium thiosulfate, optionally together with a neutralising component, is dissolved in the quantity of water necessary for granulation and the remaining components of the formulation are granulated. Alternatively, the thyroid hormone is added to the granulation liquid and the excipient mixture granulated.

After the usual drying and, if necessary, grinding methods, the substances may be processed to the desired medicaments, e.g. tablets or sugar-coated tablets, or may be filled in capsules. Liquid medicaments may be stabilised in the same manner and provided, for example, as a solution or a lyophilisate made therefrom.

The following exemplary compositions will illustrate the invention in greater detail without limiting its potential scope. All of the components used in the examples correspond to Pharmacopoeia standards.

EXAMPLE 1

| | |
|---|---|
| Levothyroxin sodium | 0.60 g |
| Pre-gelatinised starch | 225.00 g |
| Corn starch | 327.00 g |
| Microcrystalline cellulose | 334.63 g |
| Sodium thiosulfate | 3.00 g |
| Sodium carbonate | 0.77 g |
| Hydrogenated castor oil | 4.50 g |
| Highly dispersed silica | 4.50 g |

Levothyroxin is suspended in a solution prepared of water, sodium thiosulfate and sodium carbonate. A mixture of microcrystalline cellulose and the two starches is granulated together with this suspension, dried, ground and mixed with the two remaining excipients. This mixture is suitable for filling into hard gelatine capsules or pressing into tablets of varying active ingredient contents. A tablet weighing 150 mg, for example, contains 100 $\mu$g of active ingredient. The weight ratio of levothyroxin to sodium thiosulfate is 1:5. A slurry of such a tablet in 30 ml of distilled water results in a pH of 8.1.

EXAMPLE 2

| | |
|---|---|
| Levothyroxin sodium | 0.125 g |
| Pre-gelatinised starch | 37.500 g |
| Corn starch | 54.250 g |
| Microcrystalline cellulose | 52.125 g |
| Sodium thiosulfate | 2.500 g |
| Hydrogenated castor oil | 0.750 g |
| Highly dispersed silica | 0.750 g |

The medicament was prepared with water as in example 1. A 148 mg tablet contains 125 $\mu$g of levothyroxin sodium with a weight ratio of 1:2 to sodium thiosulfate.

EXAMPLE 3

Analogously to the composition of example 2, 90 kg of a granulate having a levothyroxin sodium content of 50 $\mu$g and a sodium thiosulfate content of 500 $\mu$g per 150 mg of granulate were prepared and pressed into tablets having an average weight of 150 mg. The ratio of levothyroxin to sodium thiosulfate was 1:10.

EXAMPLE 4 (comparative)

Analogously to example 3, 90 kg of a granulate without sodium thiosulfate were prepared and pressed into tablets.

EXAMPLE 5

| | |
|---|---|
| Levothyroxin sodium | 0.100 g |
| Liothyronin sodium | 0.010 g |
| Corn starch | 92.000 g |
| Microcrystalline cellulose | 54.900 g |
| Sodium thiosulfate | 0.500 g |
| Sodium carbonate | 0.900 g |
| Hydrogenated castor oil | 0.750 g |
| Highly dispersed silica | 0.750 g |

A granulate using water was prepared analogously to example 1. 150 mg tablets contain 100 $\mu$g of levothyroxin sodium, 10 $\mu$g of liothyronin sodium and 500 $\mu$g of sodium thiosulfate which results in a ratio of thyroid hormone to sodium thiosulfate of 1:4.5.

A tablet slurried in 100 ml of water resulted in a pH of 7.9.

EXAMPLE 6

Tablets as produced in examples 3 and 4 were packaged in commercial blister packs, using a PVC foil of 250 $\mu$m thickness as the bottom foil and an aluminium foil of 20 $\mu$m thickness as cover foil. Then their stability was tested in a comparative manner. The tablets were stored under the following defined conditions.

21° C./45% of relative humidity
26° C./60% of relative humidity
30° C./70% of relative humidity
40° C./75% of relative humidity The results are shown in table 2.

TABLE 2

|  | Initial value | Stored for 12 months | | Stored for 6 months | |
| --- | --- | --- | --- | --- | --- |
|  | (in % of the theoretical content) | 21° C. | 26° C. | 30° C. | 40° C. |
|  |  | (Decrease of the content compared with the initial content) | | | |
| Example 3 with thiosulfate | 102.1 | ±0% | ±0% | −0.7% | −9.5% |
| Example 4 without thiosulfate | 105.9 | −5.3% | −7.9% | −12.8% | −23.2% |

The content was determined by means of selective analysis. The results show a dramatic difference in the decrease of the content of the intact active ingredient and illustrates the stabilising effect of the sodium thiosulfate on the thyroid hormone.

Thus, the new teaching of the invention provides a simple process for preparing thyroid hormone preparations which have such a high stability even under extreme and unfavourable climatic conditions that storage without special precautions is possible while almost the full content of active ingredient is retained for therapy for markedly longer than three years.

We claim:

1. Stable medicaments containing thyroid hormones, wherein said medicaments comprise sodium thiosulfate as the stabilising component in a ratio of thyroid hormones to sodium thiosulfate of 1:0.1 to 1:50 by weight.

2. The medicaments according to claim 1, wherein the medicaments further comprise an alkaline component an amount of which can be adjusted in such a manner that the medicament slurried or dissolved in water has a pH of 5.5 to 9.

3. The medicaments according to claim 2, wherein the alkaline component is an alkali salt or a lye.

4. The medicaments according to claim 3, wherein the alkali salt is sodium carbonate.

5. The medicaments according to claim 1, the thyroid hormone is levothyroxin.

6. The medicaments according to claim 1, wherein the thyroid hormone is liothyronin.

7. The medicaments according to claim 1, wherein the thyroid hormone is diiodothyrosin.

8. The medicaments according to claim 1, wherein the medicaments contain at least two thyroid hormones.

9. The medicaments according to claim 1, wherein the medicaments contain a further active ingredient in addition to at least one thyroid hormone.

10. A method for preparing medicaments comprising:

adding sodium thiosulfate in a dissolved state to a matrix mixture containing thyroid hormones, wherein the ratio of the thyroid hormones to sodium thiosulfate is 1:0.1 to 1:50 by weight.

11. The method of claim 10 further comprising:

adding an alkaline component to the matrix mixture, wherein the alkaline component is added in an amount such that the matrix mixture slurried or dissolved in water has a pH of 5.5 to 9.

12. The method of claim 11, wherein the alkaline component is either one of an alkali salt and a lye.

13. The method of claim 12, wherein the alkali salt is sodium carbonate.

14. The method of claim 12, wherein the thyroid hormone is levothyroxin.

15. The method of claim 10, wherein the thyroid hormone is liothyronin.

16. The method of claim 10, wherein the thyroid hormone is diiodothyrosin.

17. The method of claim 10, wherein the medicament contains at least two thyroid hormones.

18. The method of claim 10 further comprising:

adding a further active ingredient in addition to at least one thyroid hormone.

* * * * *